(12) United States Patent
Page

(10) Patent No.: US 8,212,675 B2
(45) Date of Patent: Jul. 3, 2012

(54) PROXIMITY LOCATOR SYSTEM

(75) Inventor: William Page, Wellington, FL (US)

(73) Assignee: Card Logistics Properties Ltd., Hamilton (BM)

( * ) Notice: Subject to any disclaimer, the term of this patent is extended or adjusted under 35 U.S.C. 154(b) by 0 days.

(21) Appl. No.: 12/774,337

(22) Filed: May 5, 2010

(65) Prior Publication Data
US 2010/0214100 A1  Aug. 26, 2010

Related U.S. Application Data (63) Continuation of application No. 11/673,371, filed on Feb. 9, 2007, now Pat. No. 7,724,137.

(60) Provisional application No. 60/771,743, filed on Feb. 9, 2006.

(51) Int. Cl.
G08B 13/14 (2006.01)
G06T 1/00 (2006.01)
G06K 5/00 (2006.01)

(52) U.S. Cl. .................. 340/572.1; 340/5.8; 235/382

(58) Field of Classification Search .... 340/572.1–572.9, 340/5.1, 539.11, 539.12; 235/382
See application file for complete search history.

(56) References Cited

U.S. PATENT DOCUMENTS

| | | | |
|---|---|---|---|
| 3,618,059 A | 11/1971 | Allen | |
| 4,897,660 A | 1/1990 | Gold et al. | |
| 5,317,636 A * | 5/1994 | Vizcaino | 705/65 |
| 6,042,005 A * | 3/2000 | Basile et al. | 235/382 |
| 6,100,804 A | 8/2000 | Brady et al. | |
| 6,454,164 B1 * | 9/2002 | Wakabayashi et al. | 235/380 |
| 6,572,015 B1 * | 6/2003 | Norton | 235/382 |
| 6,880,752 B2 | 4/2005 | Tarnovsky et al. | |
| 6,885,288 B2 | 4/2005 | Pincus | |
| 6,980,087 B2 * | 12/2005 | Zukowski | 340/10.51 |
| 6,983,882 B2 | 1/2006 | Cassone | |
| 6,997,381 B2 | 2/2006 | Arnouse | |
| 7,424,134 B2 * | 9/2008 | Chou | 382/115 |
| 2004/0046637 A1 * | 3/2004 | Wesby Van Swaay | 340/5.1 |
| 2004/0150525 A1 * | 8/2004 | Wilson et al. | 340/572.1 |
| 2005/0050366 A1 * | 3/2005 | Kwok et al. | 713/202 |
| 2005/0052283 A1 | 3/2005 | Collins et al. | |
| 2005/0127157 A1 | 6/2005 | Stemmle et al. | |
| 2005/0207624 A1 * | 9/2005 | Ehlers et al. | 382/124 |
| 2006/0102717 A1 * | 5/2006 | Wood et al. | 235/382 |

* cited by examiner

*Primary Examiner* — Jennifer Mehmood
(74) *Attorney, Agent, or Firm* — Lee & Hayes, PLLC

(57) ABSTRACT

A Proximity Locator System for individuals includes a credit card size card which is carried in an individual's wallet. The card is provided with a wireless communication device which is used in conjunction with a locating device to locate an individual. This may be utilized to locate individuals lost at sea, in an avalanche, or under the debris of a fallen building. The communication device on the card may be solar powered or activated by a RF signal from the locator device. The card does not require a battery to power the communication device. Therefore it may be carried by and individual and activated at any time. In this manner it is fully operational when someone is attempting to locate the card. The card also contains a smart chip with vital information about the individual which can be accessed by individuals with different authority levels.

15 Claims, 8 Drawing Sheets

PROXIMITY LOCATOR SYSTEM

CROSS REFERENCE TO RELATED APPLICATIONS

This application is a continuation of application Ser. No. 11/673,371 filed Feb. 9, 2007. Application Ser. No. 11/673,371 claims the benefit of U.S. Provisional Application No. 60/771,743 filed on Feb. 9, 2006. The entire disclosures of the prior applications are herein incorporated by reference.

FIELD OF THE INVENTION

Recent disasters such as hurricane Katrina and the terrorist attacks on Sep. 11, 2001 have clearly illustrated a need to be able to quickly locate a large number of people were stranded, trapped or even killed. This need could be satisfied by the use of a Proximity Locator System (PLS) which includes a portable device that could easily be carried on one's person. The Proximity Locator System, in addition, could also contain personal identification information and vital medical information. In the event the rescued individual was unable to provide any information, this information could be accessed by authorized individuals and used to identify the individual and provide proper medical treatment for the individual.

BACKGROUND OF THE INVENTION

Whenever an individual is lost the first and most significant problem is how to locate the individual. Today most individuals who go into wilderness areas carry Global Positioning System (GPS) devices and cellular of satellite phones. If the individual becomes lost or injured they can use the GPS device to determine their longitude and latitude and then call for help on their phone. With the longitude and latitude information the rescue team can quickly locate and recover the individual. Not everyone that enters the wilderness has a GPS device and cellular or satellite phone with them. Should them become lost or injured the authorities are not notified until the individual fails to return at a preselected time to a specific location. The individuals who contact the authorities may or may not know the approximate location of the lost individual. Also, the individual may have chosen to go to an area different from the area where he had indicated that he would be. Locating the individual becomes a very difficult task if the individual has been lost for an extended period of time or lost at sea. Until now the most widely used method of finding the individual was to send out a large number of people and visually search for the person. This is a very tedious and time consuming task. Another problem is that of human error. A member of the search party can easily overlook the lost individual if they are searching a vast area from a plane or boat.

There currently exist a number of locating devices which employ transmitters that broadcast on selected frequencies. There frequencies can be monitored by rescue personnel to assist in locating the lost individuals. These are EPIRB, Emergency Position Indicating Radio Beacon, utilized in the maritime industry; ELT, Emergency Locator Transmitter, used in the aircraft industry and PLB, Personal Locator Beacon, used by individuals in recreation of other activities. These devices require power sources such as batteries to operate the transmitters. Some of these devices are not small nor readily transportable by individuals. In addition, these devices are not normally carried by the individual unless the individual knows that they are going to areas where problems may exist.

Other problems exist if the individual becomes buried under snow or other debris. Visual identification is not possible and therefore other techniques must be employed. In these situations trained dogs or thermal sensors are used to located the lost individual. These techniques have their own limitations. Thermal sensors do not have a very long operating range and trained dogs are not always readily available nor can they be used in water environments.

There exists a need for a locating system that can be readily carried by an individual, can operate if the individual is unconscious and can provide identification and medical information to rescue personnel.

DESCRIPTION OF THE PRIOR ART

U.S. Pat. No. 6,963,283 discloses a transmitting device and a receiver used to track an individual such as a small child. The transmitting device is small, self-contained, battery powered and can be attached to a watch, a bracelet or pinned to the clothing of the child. The transmitter can be remotely activated or activated by the wearer by simply pushing a panic button. In the event a child becomes lost a parent or other adult will notify the authorities the frequency that the transmitter is operating on and satellites could triangulate the location of the child with the signals received from the transmitter. This device does not provide any medical or other identification information regarding the wearer. Also, this device must have a power source, such as batteries, to operate.

U.S. Published Patent Application No. 2007/0013525 discloses a device and method for searching for and locating a person buried alive, such as by an avalanche. A wireless transmitter carried by the buried person sends out signals which are received by a receiver. The receiver has two operational modes. The first mode is a search mode wherein the receiver determines the approximate location of the person. The second mode is a point-localization mode wherein the receiver can determine the exact position of the buried person. The transmitter does not provider the rescuer with any information regarding the identity or medical conditions of the person wearing the transmitter.

These references fail to teach or disclose a small, readily portable transmitting device which can be readily carried by an individual in accordance with the present invention. What is lacking in the art is a transmitting device which can readily be carried by an individual and does not need a self-contained power source to operate. In addition the transmitter contains information regarding the identity of the individual and medical information regarding the individual. The individual carrying the transmitting device does not have to be conscious to activate the device or for someone else to obtain the identification and medical information.

SUMMARY OF THE INVENTION

A proximity locator system has been developed that can be readily carried by an individual without the need for specialized equipment such as GPS locators or Personal Locator Beacons (PLB). The proximity locator system has three major components. The first component is a PLS card which contains an antenna, a silicon chip and a logic circuit. The second component is a locating device or receiver. The PLS card is preferably the size and shape of an ordinary credit card and can be carried by an individual in their wallet. The PLS card also preferably has a smart card chip or similar device therein. The chip contains information by which the person may be identified. Additional information such as healthcare, biometrics, financial, and telecommunications may also be stored on the chip. The third component is a card reader. The card reader is employed in conjunction with the PLS card to enable individuals to read and extract the information stored on the PLS card. The PLS card and locating device can employ an active or passive transponder.

Accordingly, it is an objective of the instant invention to provide a proximity locator system including a readily transportable transmitting and storage device and a tracking or locating device.

It is a further objective of the instant invention to provide an readily transportable locating device onto which a large variety of information may be stored and retrieved therefrom.

It is yet another objective of the instant invention to provide an readily transportable locating device with the ability to restrict access to certain information stored on the device.

It is a still further objective of the invention to provide an readily transportable locating device including a passive and/or active power supply.

It is still a further objective of the invention to provide an easily transportable locating device which is responsive to triangulation by tracking devices.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

BRIEF DESCRIPTION OF THE FIGURES

FIG. 11 is a top plan view of the transmitting and storage device of another embodiment illustrating the top layer separated from the lower layer.

DETAILED DESCRIPTION OF THE INVENTION

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

Figure 1:
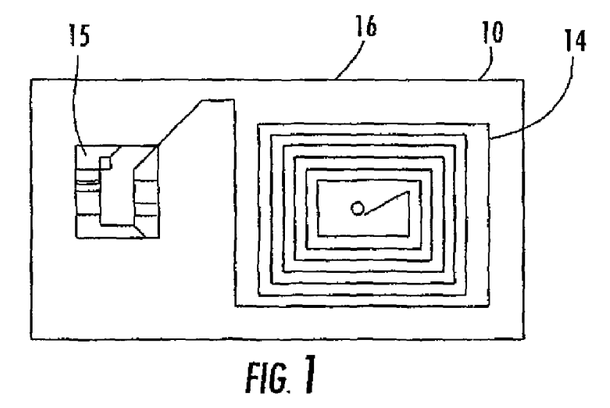
FIG. 1 is a top plan view of the transmitting and storage device of the instant invention including a smart chip and the antenna.
Figure 4:
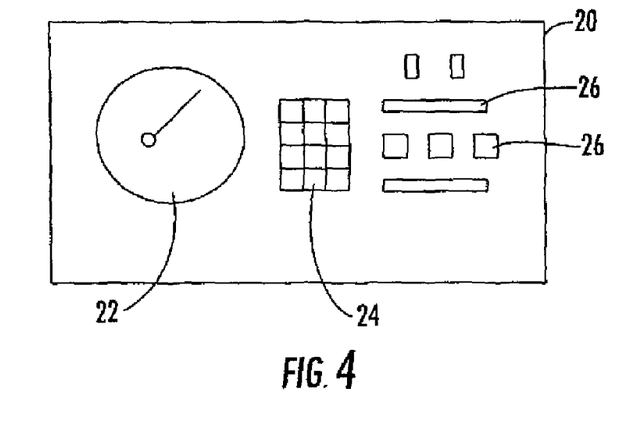
FIG. 4 is a front view of a tracking device that can be mounted in a vehicle.
Figure 5:
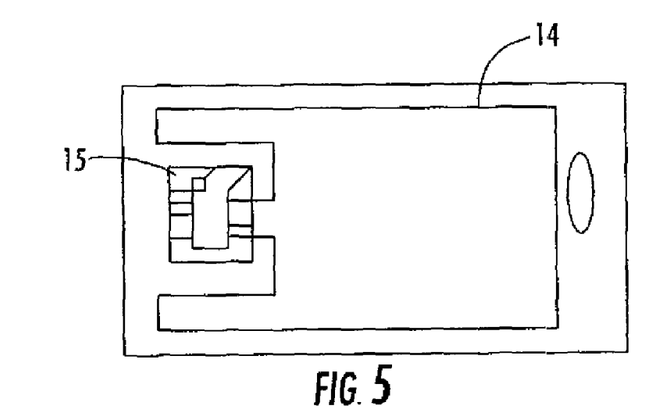
FIG. 5 is a top plan view of the transmitting and storage device of the instant invention including a smart chip and another antenna configuration.
Figure 6:
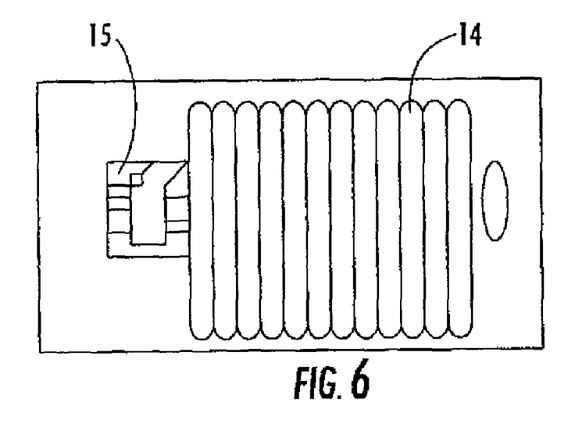
FIG. 6 is a top plan view of the transmitting and storage device of the instant invention including a smart chip and yet another antenna configuration.
Figure 7:
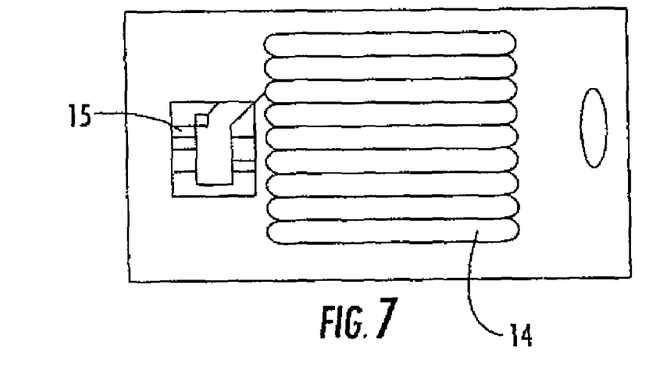
FIG. 7 is a top plan view of the transmitting and storage device of the instant invention including a smart chip and another antenna configuration.
Figure 8:
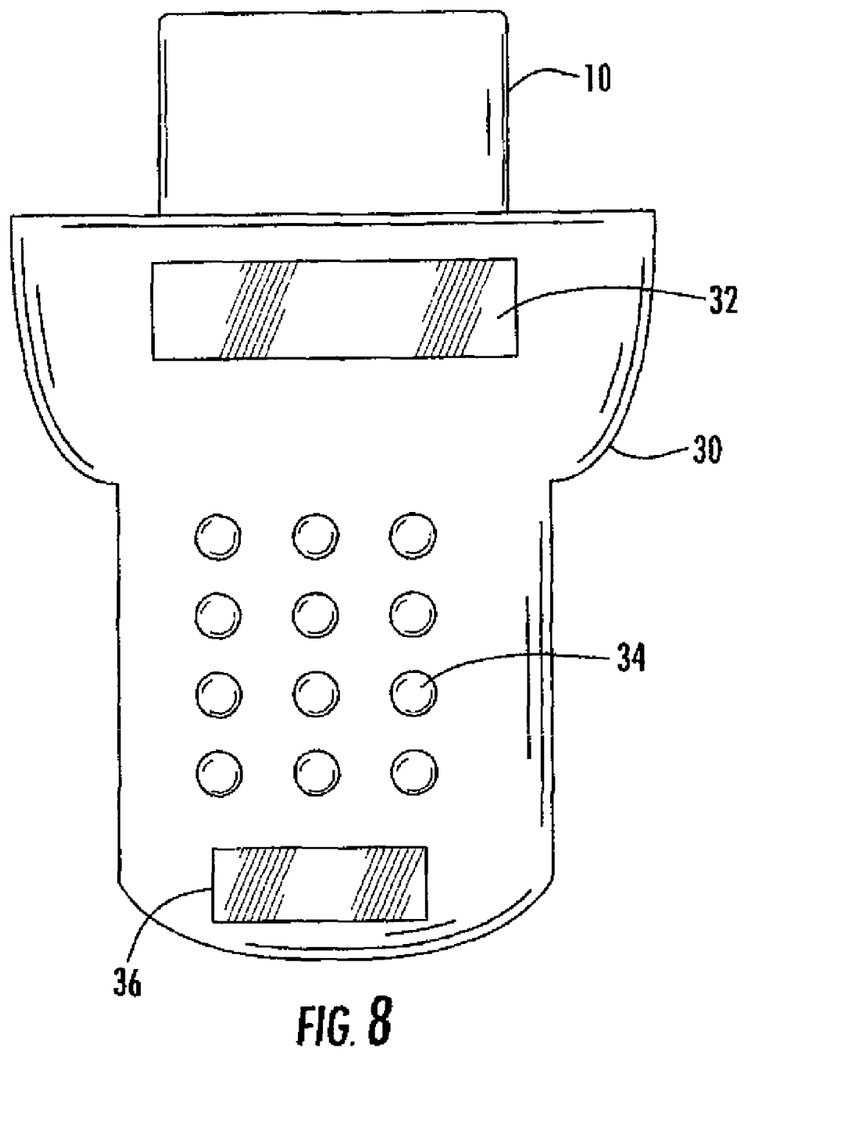
FIG. 8 is a front plan view of a card reader.

Referring now to FIGS. 1-13 the present invention is shown as a proximity locator system having three basic components. The first component is a proximity locator system (PLS) card 10 (FIG. 1) or transmitting device which contains an antenna 14, a silicon chip 12 and a logic circuit 50. The second component is a locating device or receiver 20 (FIG. 4). The PLS card 10 is preferably the size and shape of an ordinary credit card and can be carried by an individual in their wallet. The third component is a card reader 30 (FIG. 8). The PLS card also preferably has a smart card chip or similar information storage device 12 therein. A smart card is a device that includes an embedded integrated circuit chip (ICC). The chip can be either a microcontroller with internal memory or a memory-only chip. A microcontroller chip can add, delete, and otherwise manipulate information in its memory. The card communicates with a reader, either through a physical connection (a contact smart card) or a remote contactless interface (a contactless smart card). Smart card are available in a variety of form factors, including plastic cards, fobs, subscriber identification modules (SIMs), and USB-based tokens. There are two general categories of smart cards: contact and contactless. A contact smart card must be inserted into a smart card reader with a direct connection to a conductive contact plate on the surface of the card (typically gold plated). Transmission of commands, data, and card status takes place over these physical contact points. A contactless card requires only close proximity to a reader. Both the reader and the card have antennae, and the two communicate over this contactless link. Most contactless cards also derive power for the internal chip from this electromagnetic signal. Smart cards have been implemented around the globe in a number of diverse industry segments, to satisfy a number of business needs. As these markets have matured, of necessity both low level and application level smart card standards have been developed. These standards are typically written and supported by either international organizations (such as ISO/IEC and CEN) or business organizations (such as EMVCO and APTA). Exemplary smart standards include ISO/IEC 7816, ISO/IEC 14443, EMV 2000 and UTFS. However, the present invention is not limited to smart cards within such standards. The chip 12 contains information relating to the person utilizing the card. An example of this type of card is an EMedical ID Smart Card. These cards contain a smart card chip or a similar information storage medium and a device for communication with a card reader. The card reader is designed to communicate with the smart card chip or similar information storage device and provide this information to a user in an readily accessible form. The information storage communicates with the reader in a passive or active manner. A passive manner is defined herein as placing the information storage device adjacent to or within the reader. Information is then transferred to the reader without any further action or input. A active manner is defined herein as placing the information storage device adjacent to or within the reader. Information is selectively transferred to the reader based on a request by a user or other actions which control the transfer of information from the information storage device to the reader. The information transferred to the card reader may be displayed on a screen 32 located on the card reader. The card reader can communicate with other devices (not shown), such as a computer, a laptop computer or a PDA and display the information retrieved from the card on these devices. The connection options include, but are not limited to USB, CF, Serial, LAN, WAN, RS232/485 and global communications. These other devices also offer the user the ability to locate the pertinent information stored on the card and access it. These other devices may be in communication with printers or other devices (not shown) which can provide a hard copy of the pertinent information should it be required.

The information contained in the information storage device can be, but is not limited to, personal medical information, personal biometric identification information including name, address, DOB, height, weight and photographs of the individual. Medical information can include vital signs, allergies, prescriptions/medications the individual is currently taking or has taken in the past, immunizations, primary care physicians, other physicians, health/medical records, lab testing results, surgical procedures, personal medical directives, advance directives such as wills, next of kin, religion, insurance policies, financial information, driver's license, registration of vehicles, etc. Therefore, in the event of a natural disaster or other situation where all of an individual's records were destroyed they would still retain a copy of these records and could readily access, them.

The card reader 30 allows the user to input information via a keypad 34 or other input device and in turn to be provided access to certain information contained in the information storage device or smart card 10. The amount of information which could be accessed by an individual would depend on their level of authority and permissions granted by the owner of the information contained in the information storage device. For example if the owner of the smart card 10 were involved in a motor vehicle accident, the EMTs or paramedics who responded to the accident would place the victim's card in a card reader 30 and then enter their identification or authorization with the keypad 34. They may also be required to enter their fingerprint on the bio-metric detector 36. They could then request the victim's vital medical information so they could properly treat the individual.

Another type of card reader 40 (FIG. 9) can read two cards simultaneously, One of the cards 10 would be that of an individual's from which the information was desired and the other card 11 would be that of an individual authorized to access certain information from an individual's card, such as a doctor or emergency paramedic personal In this situation a paramedic, EMT or other emergency personnel would insert the card of an individual requiring medical attention into the card reader and then they would insert their own card into the reader which would grant them permission to retrieve certain medical and/or other information from the individual's information storage device on their card. Once the individual was transported to a hospital, the hospital personnel or doctors would be able to access other more comprehensive information from the individual's card. Access to a patient's clinical and administrative records can be role-based and authenticated by the smart card. The level of information access could be controlled by compliance with certain standards which may be issued by the government or other agencies. The owner of the card could also control which individuals would have access to certain information.

Figure 9:
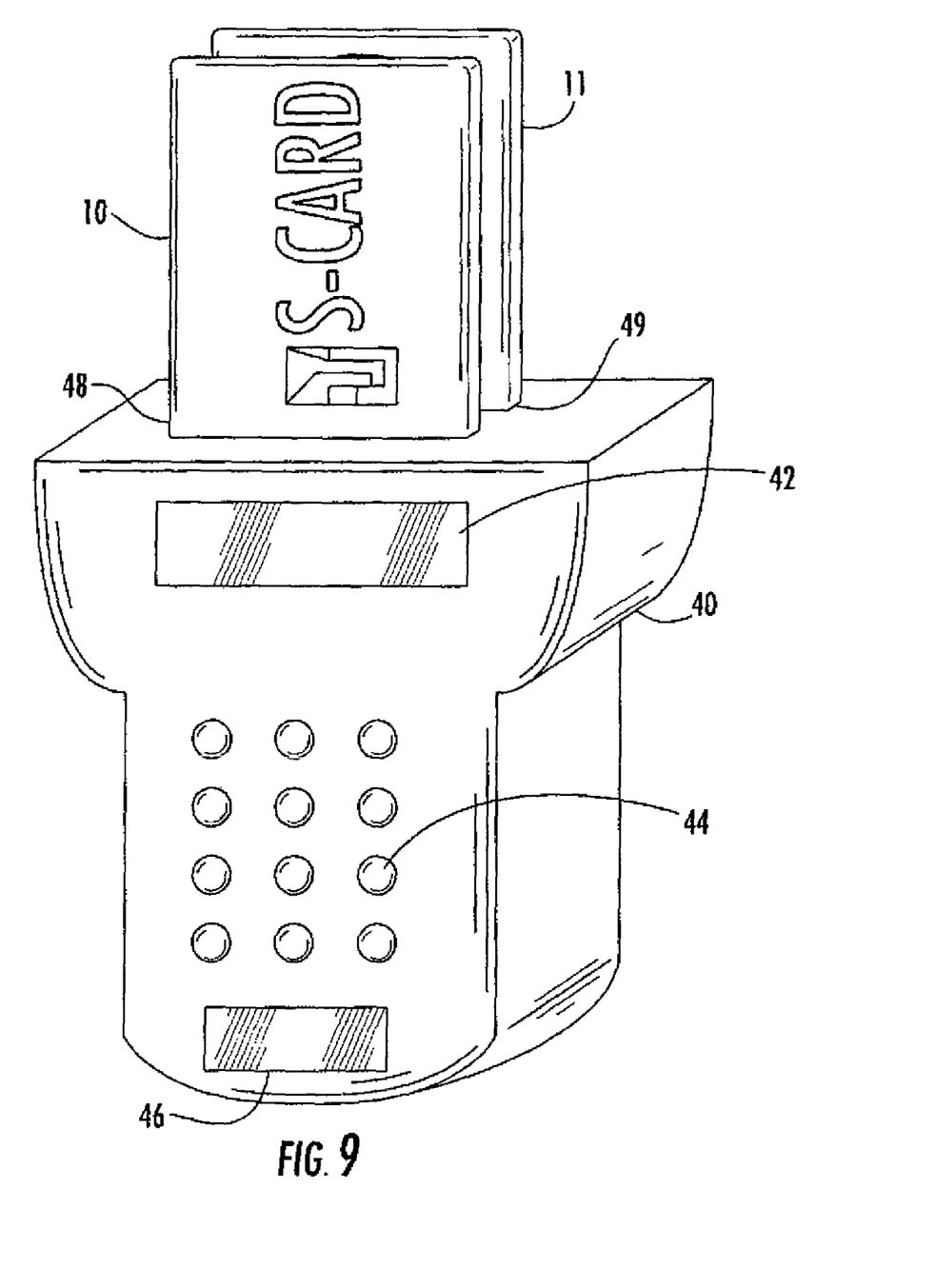
FIG. 9 is a front perspective view of a card reader which can read two cards.

In a preferred embodiment the card reader 40 has two slots 48 and 49. The reader also has a display 42, a keypad 44 and a bio-metric identifier 46. The bio-metric identifier is preferably a finger print detector. Either card reader can access the information stored on the card wirelessly or by physical contact with terminal 15 located on the card. Terminal 15 is connected to both the chip 12 and antenna 14. The card reader also contains software to control its operation. The software identifies the individual from the information on their card 10 and which individuals are authorized to access the information contained on the individual's card. When an individual first receives their card the card is preprogrammed with the individual's name, date of birth and pin-code. The card owner can then log onto the card's web site change the pin-code and authorize different individuals to have certain levels of access to the information on the card. They can also add information such as emergency contacts, advance directives, personal photos, etc. They cannot add or change medical information such as prescriptions current being taken, results of medical tests, medical records, vital signs, etc. This information can only be added or changed by authorized individuals such as physicians. This information would normally be added or changed at a hospital or primary care physician's office. Card readers which can access the card's web site would be at these locations. The individual's card could be updated or modified when placed in one of these readers and the information downloaded from the web site. If other physicians or individuals are added to the authorized list they are automatically added to the individual's card when the new person inserts their card into the card reader. All the individual's information is contained on the card. There is no need to access different databases or web sites to obtain the vital information regarding the card owner. The emergency personnel or other authorized individuals need only to insert the card into a reader, identify themselves and the information the need will be made available to them.

Practical applications and utilities of the information storage devices, such as the Smart Card, are illustrated in a paper entitled "Smart Card Applications in the U.S. Healthcare Industry", published by the Smart Card Alliance in February 2006, publication No. HC-06001, which is incorporated by reference herein in its entirety.

Figure 2:
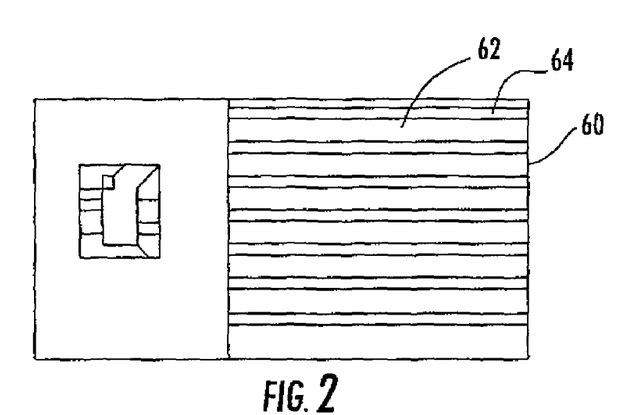
FIG. 2 is a bottom plan view of the transmitting and storage device of the instant invention including photo cells and energy storage devices.
Figure 3:
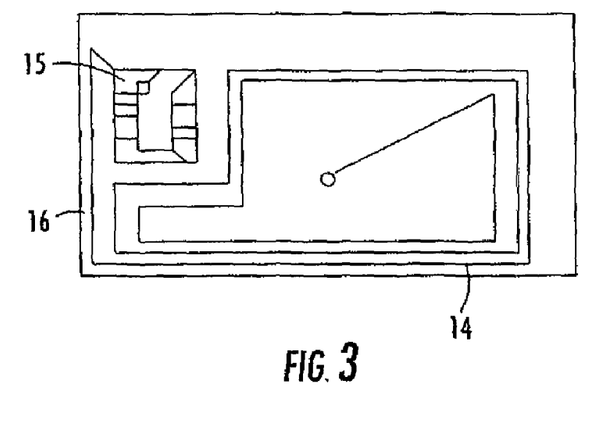
FIG. 3 is a top plan view of the transmitting and storage device of the instant invention including a smart chip and another antenna configuration.
Figure 10:
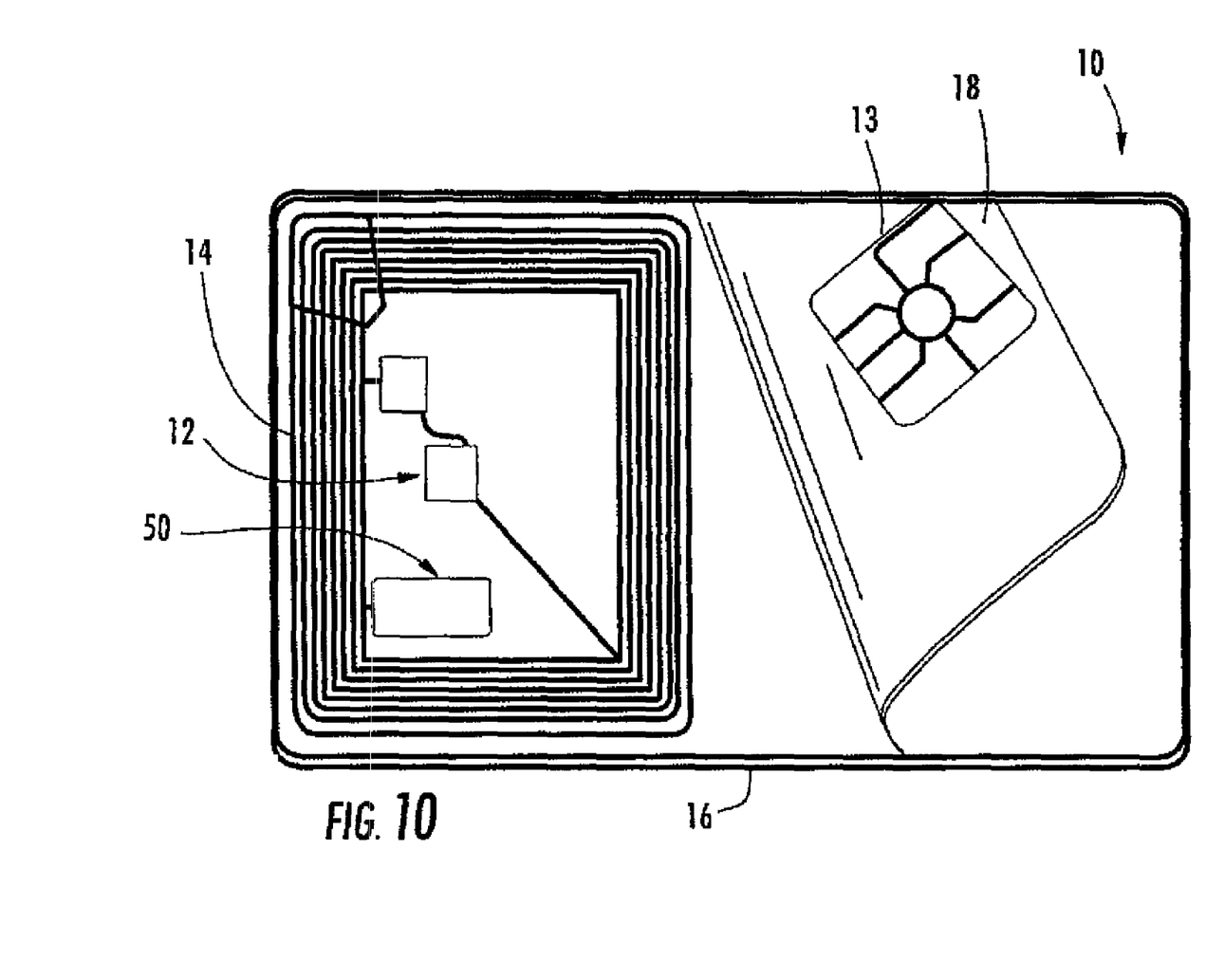
FIG. 10 is a top plan view of the transmitting and storage device illustrating the top layer separated from the lower layer.

The locator feature of the PLS card includes a radio frequency and logic circuit 50 and an antenna 14 which is incorporated into a lower layer 16 of the card. Various antenna configurations are illustrated in FIGS. 1, 3 and 5-7. The card also includes an upper layer 18 (FIGS. 10 & 11). The upper layer 18 of the card normally has a reader contact 13 and branding or indicia thereon (FIG. 10). The locator feature is activated by an active or passive power supply incorporated into the card. An example of the active power supply would be a photovoltaic generator 60 (FIG. 2). This consist of a series of photo cells 62 which convert light into electrical energy. This energy is stored in a series of capacitors 64. Both the photo cells and capacitors are thin and flexible. The thickness of these is approximately half the thickness of the card into which they are incorporated. Since they require light to operate, they cannot be covered by any opaque material. The surface of the card which contains these cells is preferably coated with a translucent coating. Under normal operating conditions it takes approximately 5 seconds to ramp or power up the locator feature. The longer the photo cells are exposed to light the more electrical energy is generated which in turn can be stored in the capacitors and provide a longer operational period of the locator feature.

Another system to activate the locator feature is a passive system whereby the antenna receives a Radio Frequency (RF) signal of a specific frequency. The distance from which the RF signal generator can activate the card is determined by the power or strength of the signal generated. The power levels and frequency rages are controlled and regulated by the FCC. Different authorities will be given permission to broadcast the activation frequencies at different power levels dependent upon the distance they would be from the individual. For example if someone were lost on the ground and the search party was on foot or ATV, the power level at which the activation signal was sent could be set to activate the card in a range of up to 100 feet. If the person was lost at sea the power level of the activation signal would be substantially higher such that the activation range was substantially greater so that the signal could be sent from a plane or ship.

Once the locator feature is activated, it can be tracked by a device 20 which will give the direction and distance of the card from the tracking device. The device 20 is provided with a screen 22 which indicates the position of the PLS card with respect to the locator. The strength of the signal can also be indicated. A keypad 24 is provided on the locator to input information by the user. Lights or other indicators 26 are also provided on the locator. These indicators can be used to indicate the strength of the signal for example. Triangulation can also be employed to establish a specific location whereby a rescue team can then be sent to that location. Since search and rescue personnel would also be carrying similar cards, their cards could be programmed to transmit a specific signal such that they could easily be identified by the tracking devices and distinguished from the lost individual.

Figure 12:
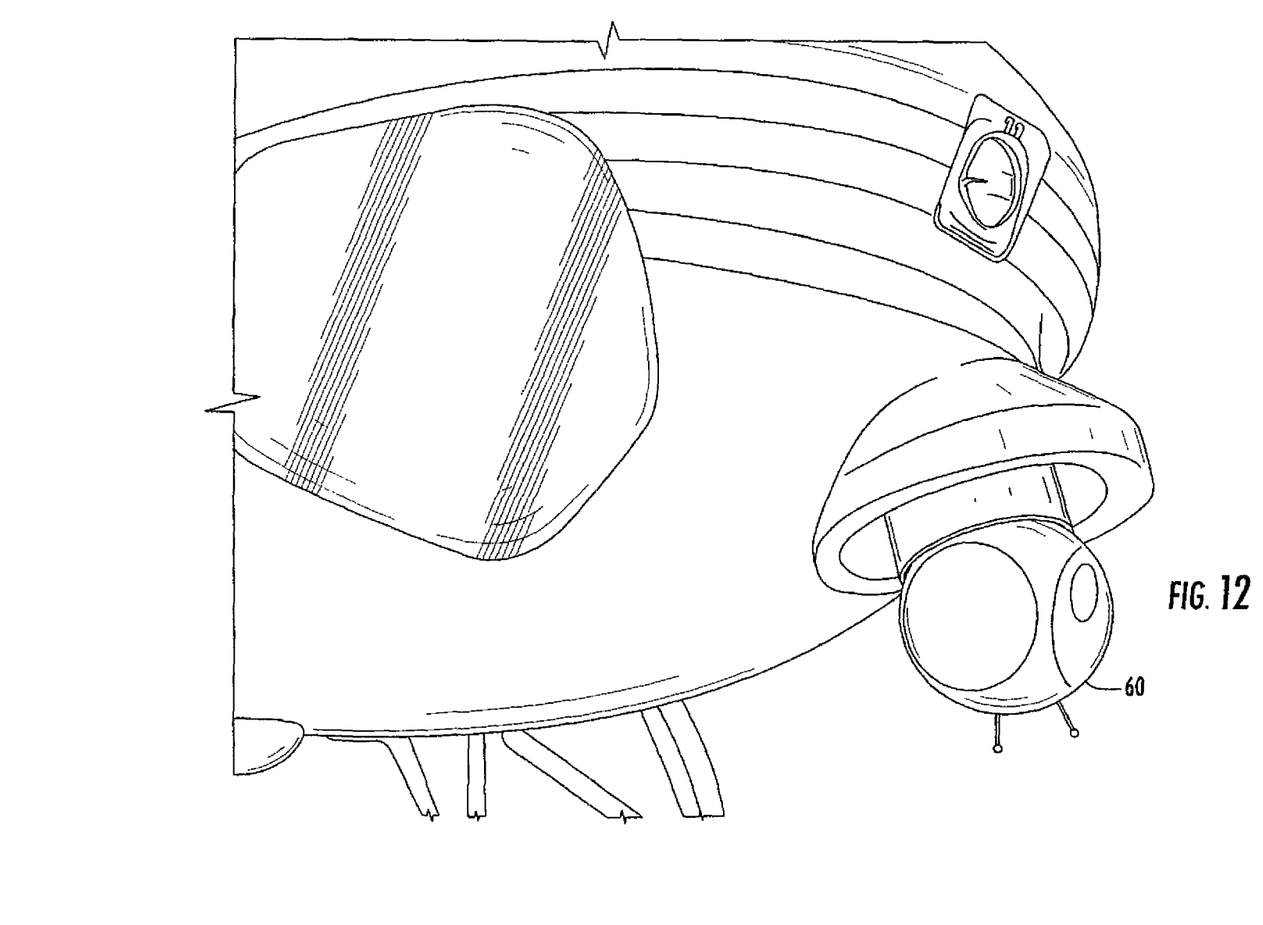
FIG. 12 is a view of a PLS receiver located on a helicopter.
Figure 13:
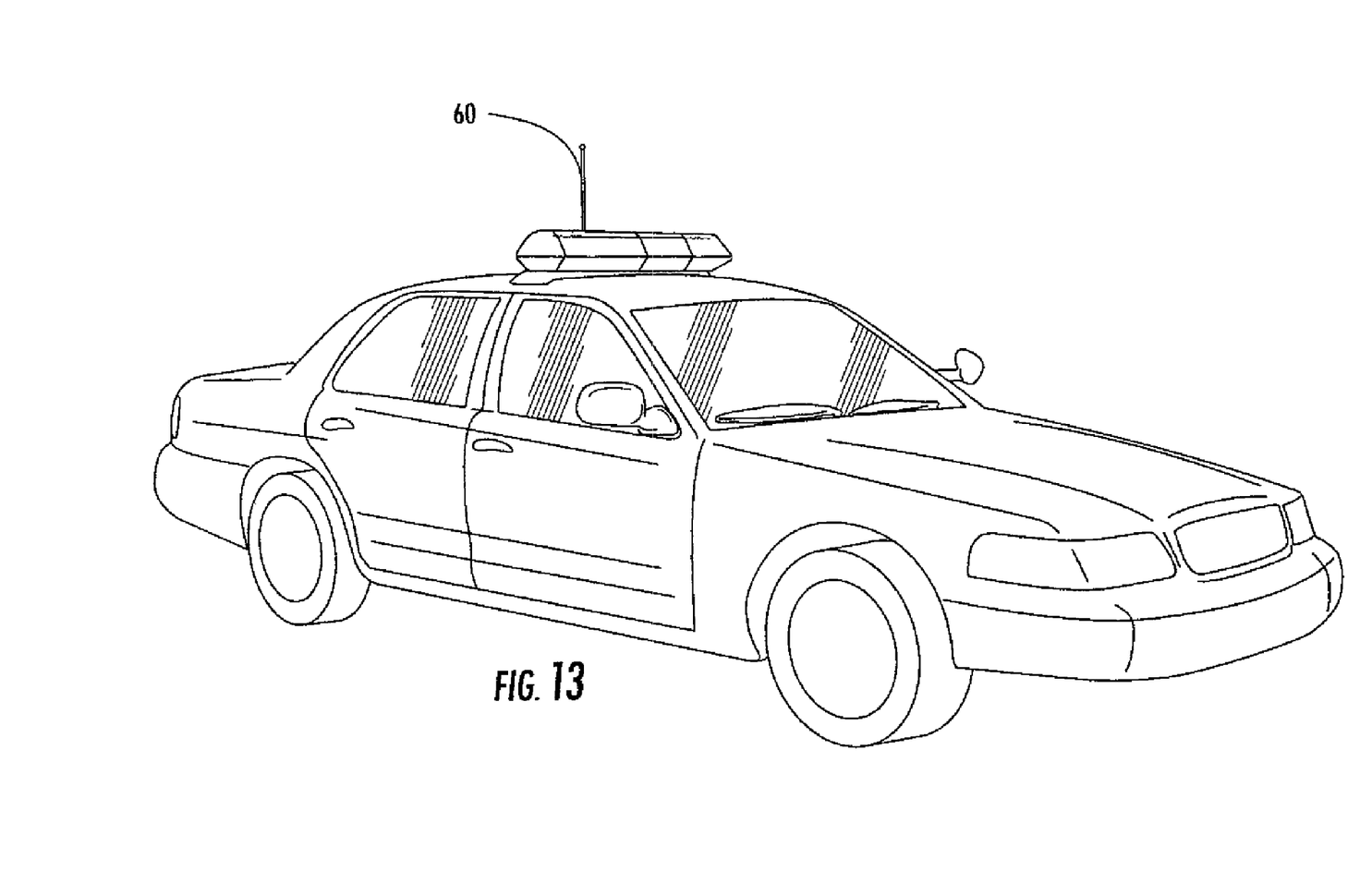
FIG. 13 is a top plan view of the transmitting and storage device of another embodiment illustrating the top layer separated from the lower layer.
Figure 17:
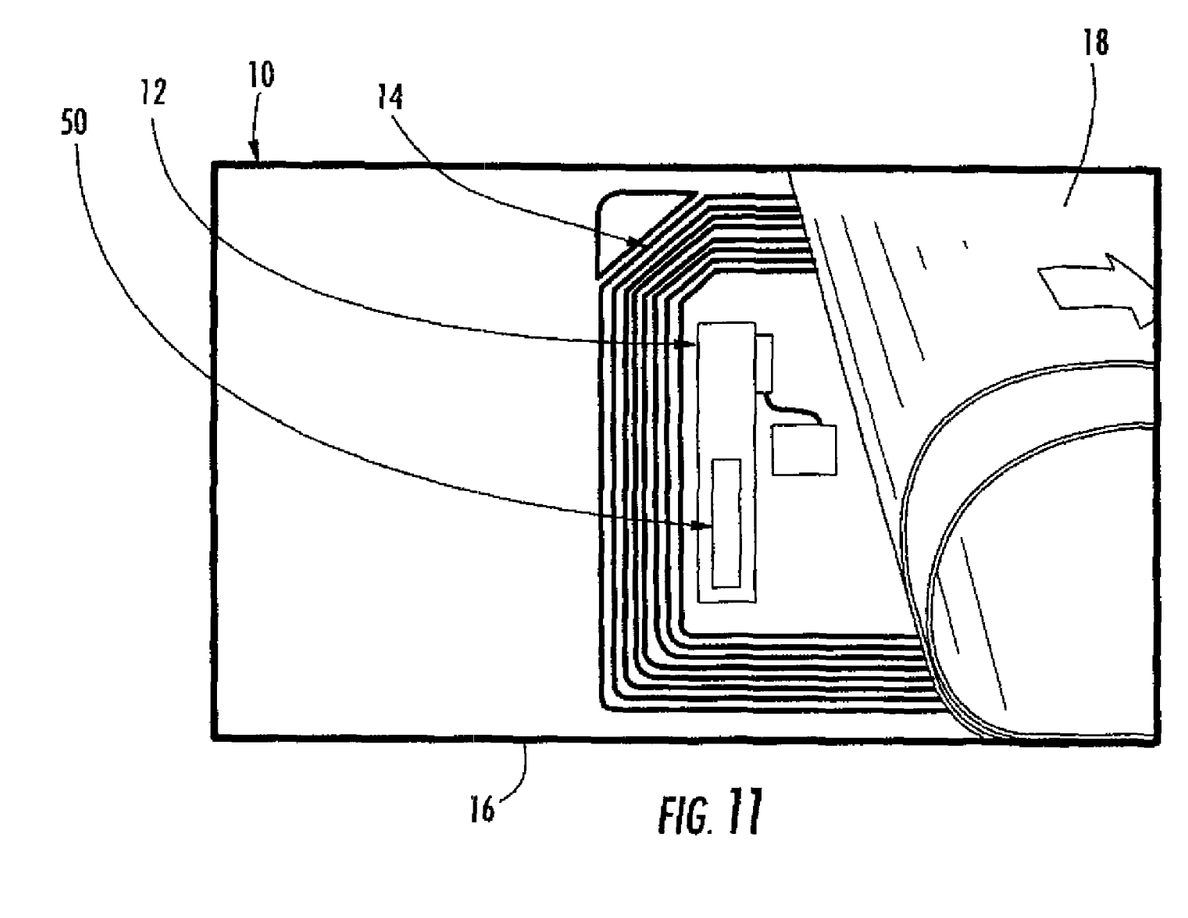

The locating device preferably employs a three point antenna system 60 which comprises three different antennae separated by approximately 120° as illustrated in FIGS. 12 and 13. These devices would normally be sized to be mounted on the exterior of a rescue vehicle. In addition a hand held unit could also be employed. Normally at least two locating devices are required to triangulate the position of an individual. However, with the proper software it is possible to only use one locating device.

The locating device can utilize Harmonic Resonance Radar or HRR. Typically HRR employs a dipole antenna and Schottky diode. The frequency at which the device is operated is dependent on the physical attributes of the aforementioned components, e.g. placement, size (inductance), etc. The operation of HRR comprises a semi directional antenna on the receiver 20 being pointed in the general direction of the person or object to be located. A radio frequency pulse of a certain duration (on time) is sent, the transmission of the pulse is stopped and the receiver enters a listening mode. In the listening mode the receiver can receive an echo from the PLS card if it is in the range of the transmitted pulse. Other types of locating and tracking systems could also be utilized.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention.

The invention claimed is:

1. A medical record storage device comprising:
   a non-transitory computer readable medium;
   a processor;
   said non-transitory computer readable medium storing medical information of an entity;
   said medical information being stored in an encrypted format on said non-transitory computer readable medium;
   said processor operating on said stored medical information;
   an interface unit adapted to interface with an external reader device; and
   said processor being adapted to communicate said medical information to said external reader through said interface unit;
   said processor being adapted to communicate said medical information to said external reader device, only when said processor determines that said external reader device is simultaneously interfaced with an authorization device which provides said external reader device with permission to access said medical information.

2. The medical record storage device of claim 1, wherein said interface unit is adapted to receive power, when interfaced with said external reader device, for powering said medical record storage device from said external reader device.

3. The medical record storage device of claim 1, wherein said medical record storage device comprises a smart card chip.

4. The medical record storage device of claim 1, wherein said medical record storage device is a SIM card comprising a smart card chip.

5. The medical record storage device of claim 1, wherein said medical information comprises a plurality of types of medical information relating to said entity;
   said medical record storage device stores a first type of said plurality of types of medical information with a first permission requirement and a second type of said plurality of types of medical information with a second permission requirement; and
   said processor being adapted to communicate, to said external reader device, types of medical information for which said authorization device can provide permission.

6. The medical record storage device of claim 1, wherein said medical record storage device is substantially the size and shape of a credit card.

7. The medical record storage device of claim 1, wherein said medical information comprises at least one of vital sign information, allergy information, information regarding one or more medications the entity is currently taking or has taken in the past, immunization information, primary care physician information, other physician information, physician visit information, health or medical record information, lab testing result information, medical imagery information, surgical procedure information, personal medical directive information, advance directive information, prescription information, pharmacy tracking information, emergency contact information, will information, probate information, next of kin information, religion information, insurance policy information, financial information, personal identification, photograph, driver's license information, demographic information, and vehicle registration information.

8. The medical record storage device of claim 1, wherein, if said processor communicates, to said external reader device, medical information stored on said medical record storage device, said processor is adapted to create a log entry on said medical record storage device identifying said authorization device.

9. The medical record storage device of claim 1,
   said processor being adapted to perform a change in said medical information stored on said medical record storage device requested by said external reader device, only when said external reader device is simultaneously interfaced with an authorization device which provides said external reader device with permission to change said medical information.

10. The medical record storage device of claim 9, wherein said medical information comprises a plurality of types of medical information relating to said entity;
   said medical record storage device stores a first type of said plurality of types of medical information with a first permission requirement and a second type of said plurality of types of medical information with a second permission requirement; and
   said processor being adapted to perform changes requested by the external reader device to types of medical information stored on said medical record storage device for which said authorization device can provide permission.

11. The medical record storage device of claim 1, wherein said entity is one of a human and an animal.

12. An information storage device comprising:
   a non-transitory computer readable medium storing information in an encrypted format;
   an interface unit adapted to interface with an external reader device; and
   a processor adapted to operate on said stored information and to communicate said information to said external reader device through said interface unit;
   said non-transitory computer readable medium further storing instructions that when executed by the processor perform operations comprising:
      determining, by the processor of the information storage device, whether to permit communication of the information stored in the information storage device to the external reader device by determining whether said external reader device is simultaneously interfaced with an authorization device which provides said external reader device with permission to access said information based on authorization information obtained from the authorization device.

13. The information storage device of claim 12, wherein said information storage device comprises a smart card chip.

14. The information storage device of claim 12, said operations further comprising:
   obtaining the authorization information from the authorization device.

15. The information storage device of claim 12, wherein said interface unit is adapted to receive power, when interfaced with said external reader device, for powering said information storage device from said external reader device.

* * * * *